United States Patent [19]
Brault et al.
[11] Patent Number: 4,895,173
[45] Date of Patent: Jan. 23, 1990

[54] SPINEBOARDS

[75] Inventors: Richard Brault; Dianne Croteau, both of Toronto; Jonathan Vinden, Mississauga, all of Canada; Ruud P. Koorn; Martin J. Spanjer, both of Hr Almelo, Netherlands

[73] Assignee: Duranamics International Inc., Toronto, Canada

[21] Appl. No.: 50,573

[22] Filed: May 18, 1987

[30] Foreign Application Priority Data

Jul. 8, 1986 [CA] Canada .................................. 513325

[51] Int. Cl.[4] .............................................. A61F 13/00
[52] U.S. Cl. ..................................... 128/870; 128/876
[58] Field of Search ............... 128/869, 870, 875, 876, 128/87 R; 5/82, 431, 432

[56] References Cited

U.S. PATENT DOCUMENTS

| | | | |
|---|---|---|---|
| 2,333,346 | 11/1943 | Sweetland | 128/876 |
| 2,675,564 | 4/1954 | Hughes | 128/134 |
| 3,535,719 | 10/1970 | Murcott | 128/876 |
| 3,650,523 | 3/1972 | Darby, Jr. | 128/134 |
| 4,024,861 | 5/1977 | Vincent | 128/134 |
| 4,124,908 | 11/1978 | Burns et al. | 5/82 R |
| 4,151,842 | 5/1979 | Miller | 128/87 R |
| 4,226,231 | 10/1980 | Anderson | 128/134 |
| 4,259,950 | 4/1981 | Klippel | 128/134 |
| 4,301,791 | 11/1981 | Franco, III | 128/134 |
| 4,506,664 | 3/1985 | Brault | 128/87 R |
| 4,612,678 | 9/1986 | Fitsch | 128/134 |
| 4,655,206 | 4/1987 | Moody | 5/82 R |
| 4,716,607 | 1/1988 | Johansson | 5/82 R |

*Primary Examiner*—Robert A. Hafer
*Assistant Examiner*—Charles H. Sam
*Attorney, Agent, or Firm*—Nixon & Vanderhye

[57] ABSTRACT

This invention relates to a spineboard and parts thereof adapted for securement and transport of a person who may have suffered a spinal injury. The spineboard consists of a board having at least one longitudinal track adapted to receive in slidable connection at least one body harness and having means to secure a head harness; at least one body harness having a pad adapted to lie over the track and having at least one strapping means adapted to engage the track in slidable connection and to encircle and to secure a person to the board; and a head harness adapted to be located on the board.

11 Claims, 6 Drawing Sheets

SPINEBOARDS

FIELD OF INVENTION

This invention relates to emergency equipment adapted to transport and secure a person who has suffered an accident. In particular, this invention relates to a spineboard and parts thereof adapted for securement and transport of a person who may have suffered a spinal injury. The invention also includes a method of production which has utility for the construction of a variety of devices in which a long rigid plastic panel is required.

PRIOR ART

The spineboard most commonly found in use today consists of a flat plywood stretcher having slots about its perimeter adapted to receive straps for immobilizing the person being carried upon it. A plywood stretcher has the advantage of cheap construction, rigidity and durability. However, it has the disadvantages that it has little buoyancy to support a victim in water, it is not of a standard size to fit all conveying means, it is uncomfortable and considerable skill and time is required to immobilize a victim on it with the straps and slots usually provided.

Another type of spineboard which has been offered in the prior art comprises a plastic moulded board called the "Millar Body Splint". This spine board provides a strapping system using fabric connectors (sometimes called VELCRO). It has been observed in tests done by Transport Canada that this board achieved complete immobilization of the body in a face-up position. However, other positions for the head were tried and the board was not adaptable to new positions. The strapping system was found not to be very reliable and the chest strap was found to be constrictive and a hindrance to CPR. It was observed that the head immobilization system had a chin strap which increased the possibility of a victim choking on regurgitated material. The head pad also restricted access to the ears which was considered to be important in head injury cases. Finally it was found that the board was not adjustable for different size victims such as children and adults.

Also in the prior art is a spineboard which is the subject matter of U.S. Pat. No. 4,506,664 to Richard A. Brault, an inventor named herein. The spineboard described in this patent comprises a fiberglass spine board adapted to immobilize a prostrate patient having a body restraint harness which consists of two lengths of flexible material each having a proximal end retained on the board at or adjacent to centre of the width thereof. Each length of the harness has a sufficient extent to extend from the proximal end in the first direction around the body of the patient to be secured to the board adjacent to side edge of the board removed from the proximal end. The body restraint harness is slidably mounted on the board so as to be positionable at any required point along the length of the patient. The body restraint harness also includes a shoulder harness and a head harness for immobilizing the patient. To facilitate the mounting and release of the dispal end of each length of the harness, the side edges of the board are formed with a mounting edge over which the hooks located at the end of the harness may hook. The board is formed with buoyancy compartments which serve to make the board horizontally buoyant in water.

It has been found, however, that the shape of this spineboard makes mass production by machines difficult and to date it has only been manufactured by hand. The board has also been strengthened to provide greater rigidity and comfort. Further, the strapping means has been improved upon to provide greater flexibility, comfort and securement. These and other advantages of the present invention are discussed in more detail below.

OBJECTS OF THE PRESENT INVENTION

It is an object of this invention to provide an improved spineboard which is capable of mass production by machine methods of manufacture.

It is an object of this invention to provide a method of manufacture that produces a plastic board of high rigidity which is required to support the spine of an injured person during transport and which has a concave upper surface to facilitate securement, handling and comfort.

It is an object of this invention to provide a spineboard that will have an improved head immobilization means. It is an object of this invention to provide an improved body strapping means that permits secure immobilization of a person on the board by more than one method depending on the nature of the injury, including the option of over the shoulder chest securement.

It is an object of this invention to provide an improved modular strapping connector system which facilitates very quick and effective immobilization and is adaptable to large or small people.

It is an object of this invention to provide a cushioned and adjustable strapping system that allows the positioning of cushioned pads beneath the person's areas of greatest pressure on the board and permits the strapping to be thereby adjusted to secure the particular portions of the person's body supporting him on the board.

It is an object of this invention to provide a board having sufficient flotation to float a person in water to facilitate water rescues.

It is an object of this invention to provide a spineboard which is adapted to fit within or on most standard transport litters of ambulances, heliocopters, ski patrols and hospitals so as to reduce the need for transferring the person from one spineboard to another during transport.

It is an object of this invention to provide a spineboard which is substantially x-ray transparent and compatible to CT signals and Magnetic Resonance Imaging.

These and other objects of this invention will become apparent upon reading the full specification.

INVENTION

The present invention may be described generally as being a spineboard comprising;

(a) a body supporting board having a length and width adapted to support a prostrate person, said board having at least one set of longitudinal tracks adapted to receive in slidable connection at least one body restraint harness and having location means to secure a head harness;

(b) a head harness comprising at least three straps attached to a forehead pad, said straps being adapted to be secured removeably to said location means of said board, said harness being adapted to be tightened over and about the head of said person to limit movement of the head without interfering with movement of the chin.

(c) at least one body harness comprising a pad adapted to lie over a set of longitudinal tracks on the board and at least one strap being adapted to engage slidably through said pad and said set of tracks of the board to permit the strap to be slid with said pad longitudinally along the set of tracks to a predetermined location while allowing the strap to be secured to the board by means of engagement through the set of tracks.

The body supporting board of this invention is adapted in preferred embodiments to fit most conventional litters of emergency transport vehicles in the area. It is believed that the preferred embodiment described herein is of such configuration for most North American transport vehicle litters and it is believed that it will be suitable for many in other places as well. It will be appreciated that some variations in the design of the shape may be desirable to meet particular local requirements.

In preferred embodiments the board will have an upper surface which is concave about its longitudinal axis and which thereby tends to increase stability of the person on the board while permitting bearers to get their fingers under the sides of the board to lift it.

The board of this invention is preferably a plastic board, and in particular embodiments is a hollow plastic shell which may be filled with a flotation material such as foam. The preferred embodiment is a hollow molded shell of polyethylene filled with a polyurethane foam. The shape of the board in the preferred embodiment has been designed to permit rotomolding, blow moulding or other known manufacturing methods to be used readily for production. Such methods allow use of high performance materials with comparatively economical and reliable replication.

An important and difficult design problem which had to be solved for use of such materials and methods was the requirement for high rigidity in a relatively thin board. A spineboard should demonstrate minimal bending along its length when it is picked up from either end even with a large adult being on it. It was found that a polyethylene board filled with foam had substantial rigidity but was not sufficient to meet the high standards of some international distributors of hospital equipment such as Ferno Washington Inc. of Wilmington, Ohio. As a result, a method of manufacture was developed wherein the hollow shell was rotomolded and cut at either end to permit the insertion of at least one, preferably two longitudinal stiffening beams having two opposing external carbon fiber faces separated by a layer of poly vinyl chloride foam. After insertion of the beams, the ends of the board were capped and the board was foamed in the conventional manner. It will be appreciated by those skilled in the art that beams might be constructed of other materials, however, it is believed that the present construction provides particularly desirable characteristics for this end use, namely high strength, light weight and compatibility with other materials and methods of manufacture and substantial transparency to x-rays, CT signals and Magnetic Resonance Imaging.

The head harness of this invention has a pad adapted to fit over the forehead of a person without obstructing the mouth, nose or ears. It is preferred that the pad be secured to the board by three straps which are located at predetermined locations on the board. The locations in the preferred embodiment comprise holes in the board which allow each strap to wrap about a portion of the board and to be connected thereto. The locations are near to the center and top of the board above the victim's head and at each side of the head laterally adjacent the lower part of the head or neck. These locations provide a tripod base from which it is possible to secure substantially the head against movement. Securement is attained by gradually increasing the tension in each of the straps until the desired immobilization of the head is obtained by the headpad on the person's forehead pressing the head towards the board.

In preferred embodiments the headpad is fabricated from a strong but elastic material that stretches slightly under the application of tension on the straps. This permits tension to even out through the headpad and to remain to secure the head even if there is a slight slackening in the straps. It is also preferred that a small oval opening be cut in the headpad. Under tension the opening expands over a portion of the head and to compress scalp and hair within it to anchor the headpad on the person's head.

In order to obtain a underlying base for securement of the head on the board and to reduce discomfort of the person, a cushion is provided on the board to support the head. In the preferred embodiment the cushion is removeably secured by straps extending through holes in the board for that purpose.

The cushion is sufficiently soft to provide a distribution of the downward load over the back of the head to avoid having the downward force being located at a point where the skull rests on the board. This reduces discomfort and provides a better base for the forehead pad to use to resist turning movements exerted on the head. In some embodiments it has been found that a wedge shape or a concave shape under the neck or above the head near the point where the skull meets the board will provide additional resistance to movement. The extent to which such devices are used will depend on the nature of the injury and the requirements at hand. Ordinarily the head cushion should be designed to provide an adequate base while presenting as little obstruction as possible to loading or unloading the victim. In this invention the board could be equipped with a number of interchangeable headpads that could be used as appropriate for the conditions at hand.

The body harness of this invention provides a pad adapted to lie over the board and under the person to provide a distributed base upon which securement can be located to avoid points of loading which are easier to move and which are more uncomfortable. These pads are not in themselves secured to the board but are adapted to receive a strap through a loop in the underside of the pad, which strap then passes into one of the set of tracks, under the board, up through the other of the set of tracks and through a second loop on the underside of the pad. By this means the pad lying over the longitudinal tracks on the board can slide to desired locations on the board. Also, by this means, when the strap is pulled during securement of a person, the force is transmitted to the board directly by the engagement of the strap with the board through the tracks. This is believed to be a substantial improvement over the strapping system developed previously by one of the inventors herein and disclosed in U.S. Pat. No. 4,506,664.

The straps of the body harness secure a person quickly and effectively. The person to be secured is placed on the board over the central portion of each strap which is fitted through the board. Each end of a strap has a slidable connector means. The ends are passed over the person in opposite directions and attached to opposite sides of the board. Then each end of the strap is pulled through its respective connector means until the strap is snug about the victim. The ends are pulled through the connector means in the same manner that a seat belt is tightened after connection is made at the buckle. Reversing the direction of the strap through the connector is possible until a catch is released on the connector means. It will be appreciated by those skilled in the art that many forms of such connectors may achieve these functions. It is preferred that the connector include a clamp adapted to fit over and be fixed on the edge of the board. A snap on clamp is preferred so that it may be easily removed when required but resists accidental dislodgement by reason of variable tension in the straps because of the person's breathing or other movement. Particulars of a preferred embodiment are discussed later.

Ordinarily there would be three body harnesses located at different positions along the board near the shoulders, buttocks and lower legs of the person. Ordinarily, three sets of tracks are provided spaced longitudinally along the board to provide a range for each of the body harnesses that would be required to secure a wide range of size from children to adults. With small children, it may be necessary to use more than one body harness in one set of tracks.

The sets of tracks are spaced apart longitudinally to improve torsional rigidity and strength of the board over the case where one track is used along the full length of the board.

In use the body harness may be located at appropriate positions, the person placed on the board on the body harness pads, the straps criss-crossed over the person to be secured on the edge of the board, then the straps may be pulled snugly through the connectors to secure and immobilize the person.

All cushions, pads and straps are preferably made of material that is easy to clean to medical standards. In the alternative or in addition the pads and cushions may be removeable and disposable. Cushions and pads will preferably be made of a material having a sufficient coefficient of friction to resist slippage between the victim and the board during securement.

In the figures which illustrate the preferred emodiments of the present invention;

In the figures which illustrate this invention, like numerals represent like elements.

Figure 1:
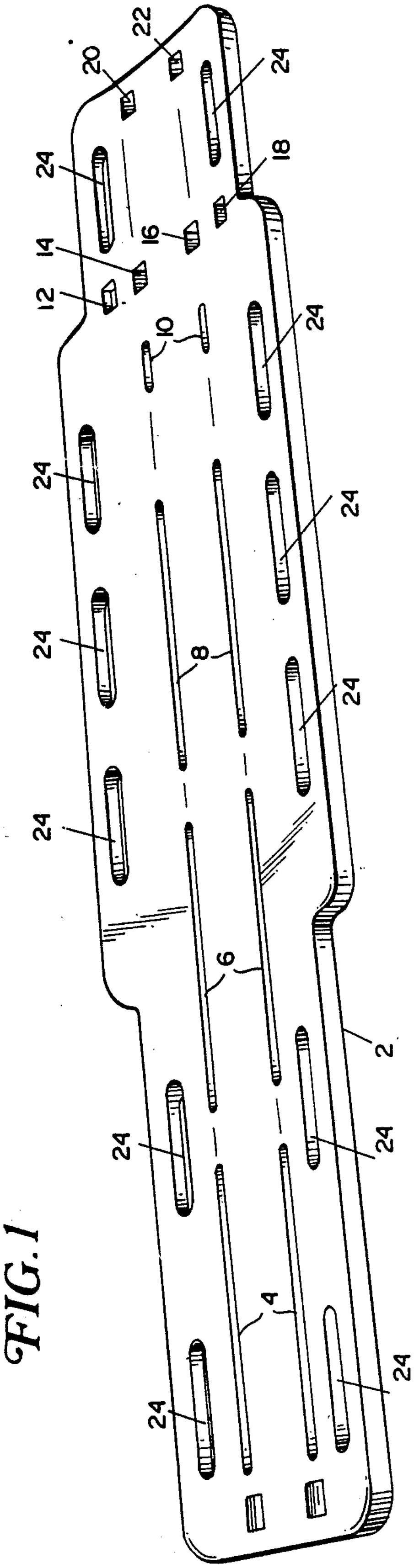
FIG. 1 is a sketch illustrating the top of the spinalboard of this invention.

As illustrated in FIG. 1, the spineboard (2) of the preferred embodiment of this invention comprises a plastic moulded exterior with a foam filled core. Particularly, a rotomoulded hull is shown. Disposed centrally along the length of the board are four sets of tracks (4), (6), (8) and (10). Each of the sets (4), (6) and (8) are adapted to receive a body harness pack in slidable connection so that it may be located at any position along the length of each set of track thereby permitting the body harness packs to be adjusted to the length of the body of the particular victim. The tracks (10) are much shorter and are positioned to locate the body harness securing the shoulders near the head harness. Less range of adjustability is required to locate the shoulders to the head whether the victim is a child or an adult. The head harness (not shown here) is adapted to be located in the openings (12) and (14), (16) and (18), (20) and (22). Each of the three straps of the head harness is located by passing through the board in one of the respective pairs of openings. The openings (12) and (14), (16) and (18) may also be used to effect over the shoulder securement as will be described later.

Along each side of the spineboard are a number of openings (24) adapted as handholds for porters.

The handholds (24) are located in slots (28) which are adapted to provide an additional underside gripping location for porters along the whole length of the spineboard (2).

Figure 2:
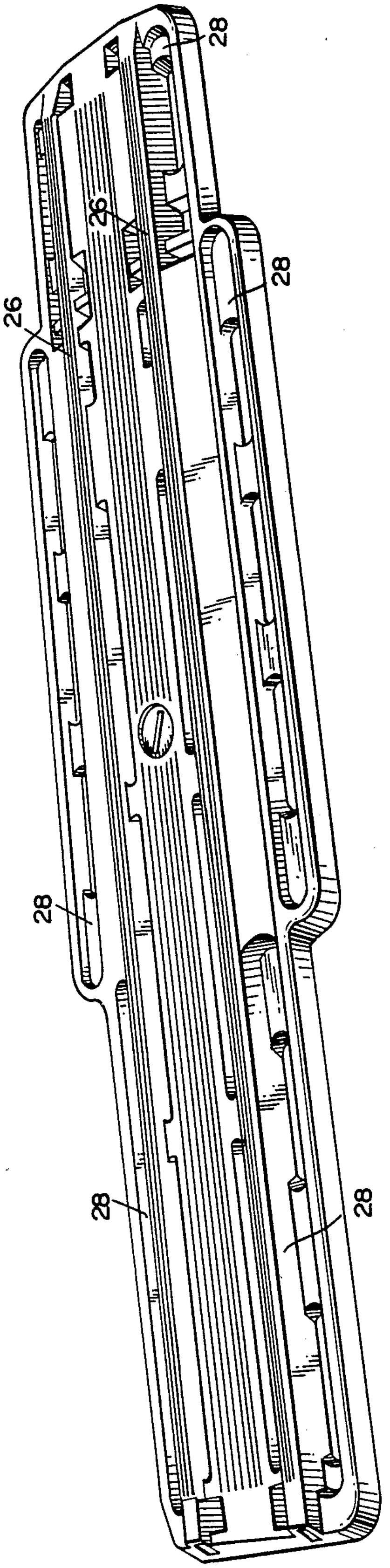
FIG. 2 is an illustration of the underside of the spinalboard of this invention.

As illustrated in FIG. 2, the underside of the board has two raised portions adapted to serve as runners (26). The raised runners (26) also provide internally a position to locate stiffening beams which are described later.

Figure 3:
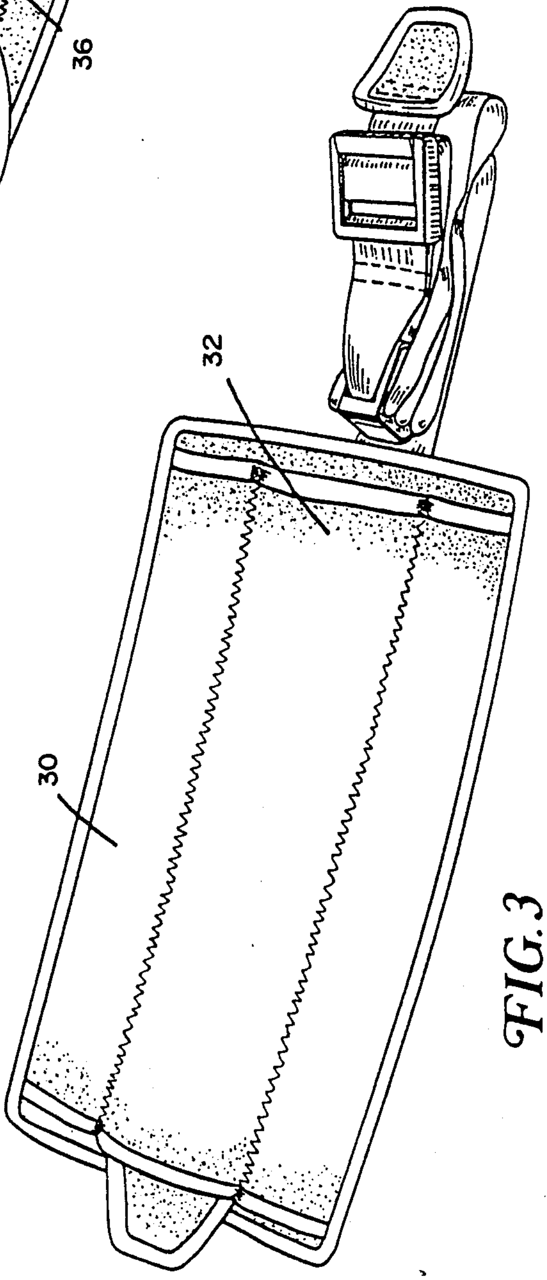
FIG. 3 is an illustration of a typical body strapping pack of this invention.

FIG. 3 shows the body harness packs including a padded cushion (30) having within it a pouch (32) adapted to receive a strap (34) within it for storage. The cushion pad (30) is adapted to lie between the victim and the board at a point of pressure to relieve against sores and discomfort caused during transport and to provide a base for securement.

Figure 4:
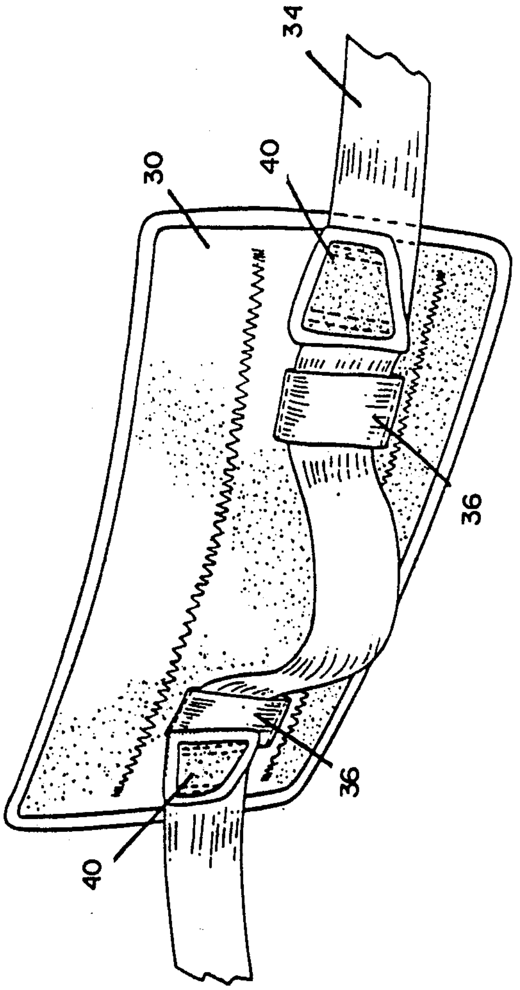
FIG. 4 is an illustration of the underside of the body strapping pack of FIG. 3.

As illustrated in FIG. 4, the strap (34) passes beneath the cushion pad (30) through loops (36). The strap (34) is adapted with tapered stops (40) which lie outside each loop (36) to restrict movement of the strap back and forth after it has passed through the loops (36).

Figure 5:
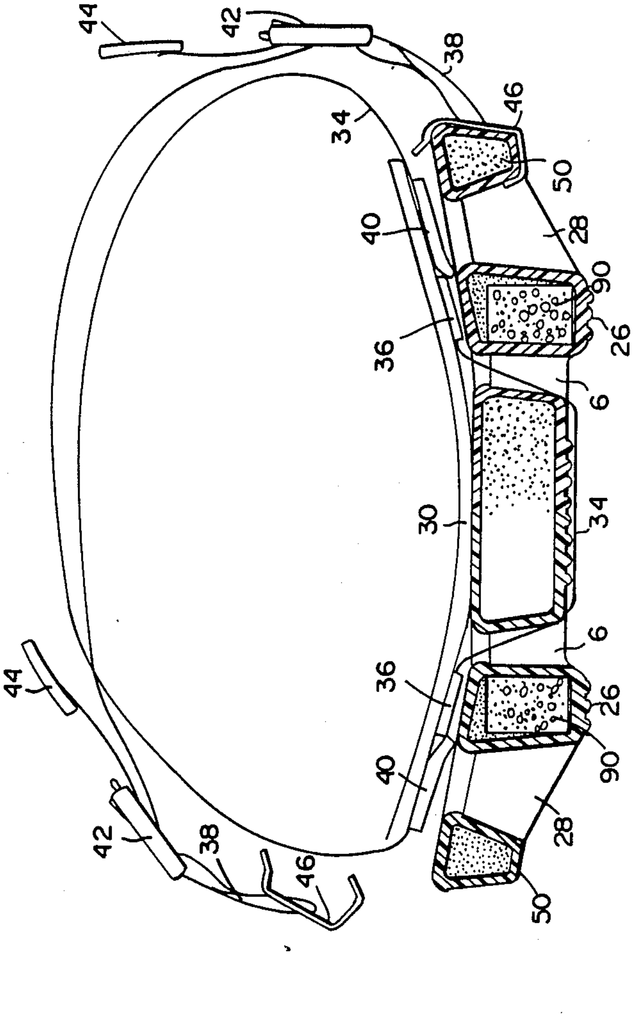
FIG. 5 is a view taken across the cross-section of the board illustrating the method of connecting the body strapping pack to the spinalboard.

FIG. 5 depicts the strap (34) in the position where the body harness is connected to the board through track sets (4), (6), (8) or (10). In FIG. 5 the slots (6) are shown in the cross-section. It will be seen that the cushion (30) lies on the top of the board over the track (6) and the strap (34) passes along the underside of the board through the slots (6). The remainder of strap (34) has two ends adapted to encircle a person lying on the board. Each end of strap (34) passes through a slidable buckle (42) and terminates in a stop (44). The slidable buckle (42) is also connected by a short strap (38) to a hook (46) which is adapted to fit over the outermost edge (50) of the spinalboard (2) in a snap fit connection.

Figure 6:
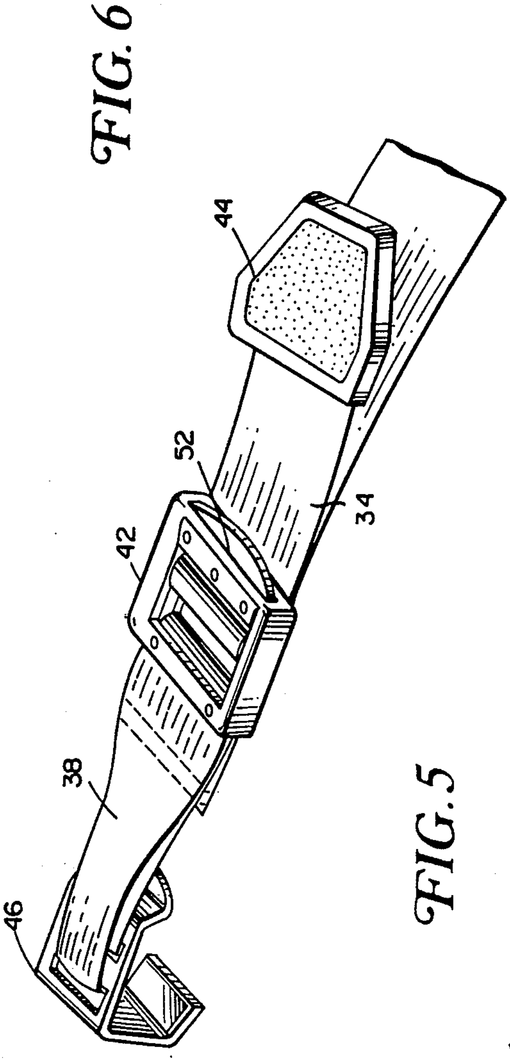
FIG. 6 is an illustration of the buckle and connecting hook of the body strapping pack harness.
Figure 7:
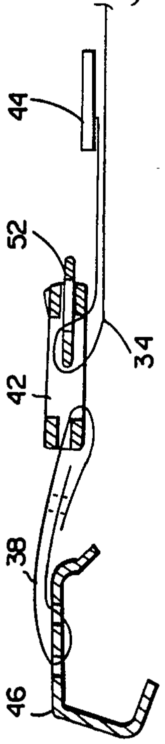
FIG. 7 is an illustration through the cross-section of the buckle and the hook to illustrate the strap connection.

A further detail of the buckle arrangement is found in FIGS. 6 and 7. It may be seen that buckle (42) contains a slidable fastener (52) about which the strap (34) is looped, (See particularly FIG. 7). Accordingly when the stop (44) is pulled strap (34) slides freely through the buckle (42). When the strap (34) is tensioned the slidable member (52) secures the strap (34) within the housing of the buckle (42) to prevent reverse slippage. Accordingly, the buckle (42) permits the strap (34) to be pulled snugly about a person by simply tugging on stop (44) after hook (46) has been fastened to the edge (50) of the board (2).

Figure 8:
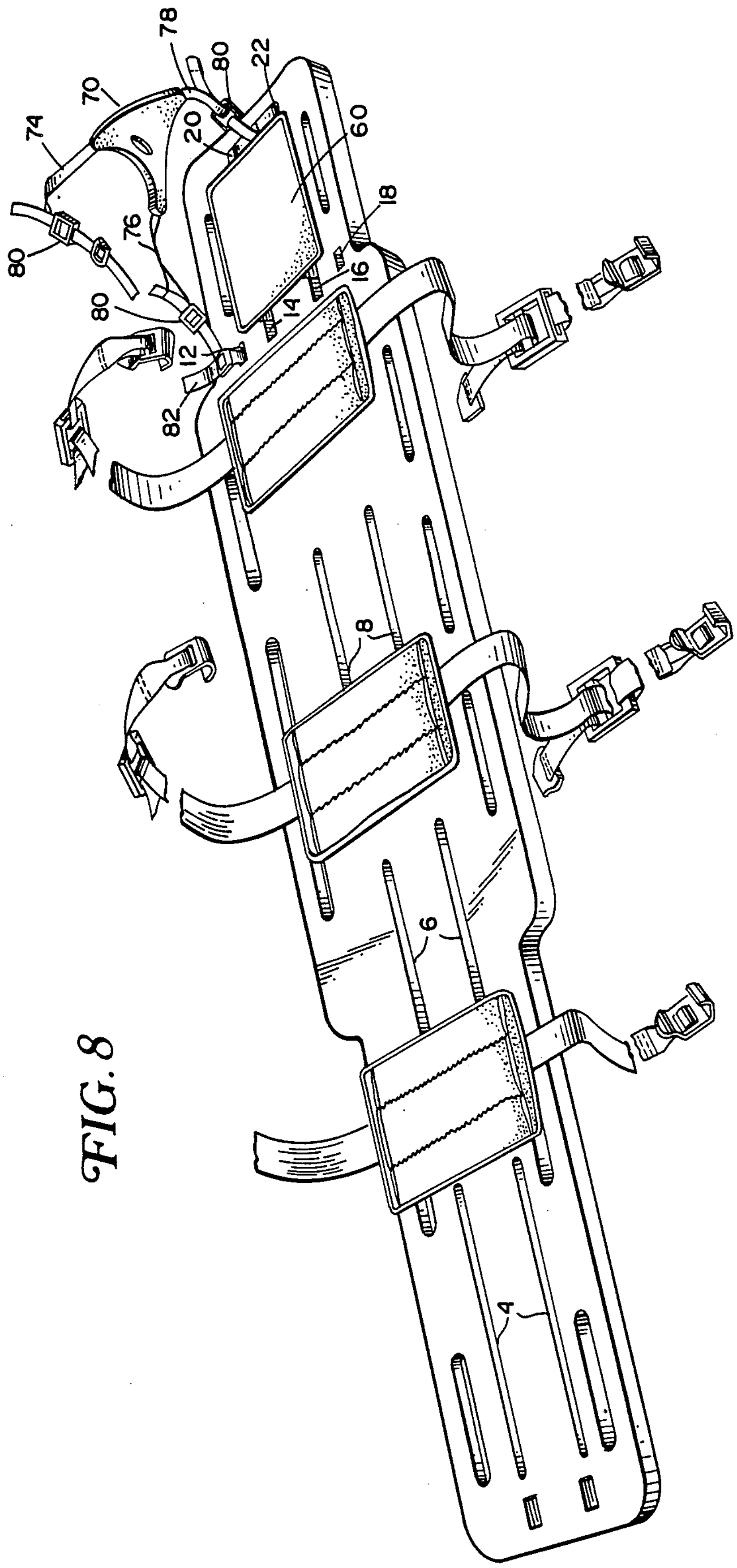
FIG. 8 is a top view of the spinalboard of this invention having mounted upon it three body packs and the head harness.

FIG. 8 shows two body harness packs positioned at various places along the tracks (6) and (8). The shoulder body harness pack is located in slot (10). Tracks (4) are not in use.

Figure 9:
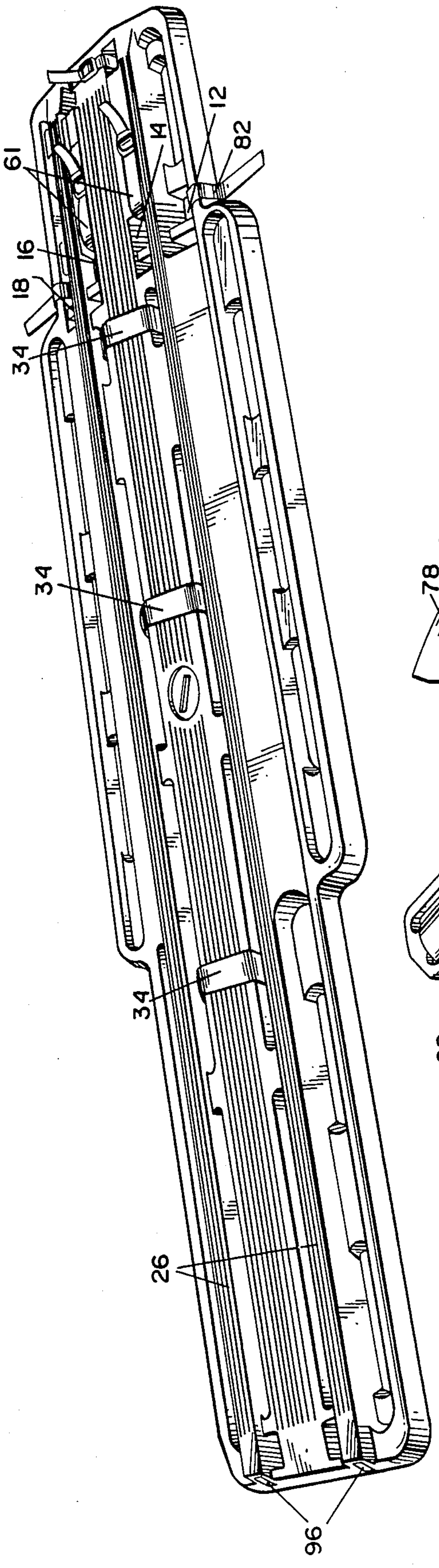
FIG. 9 shows the underside of the spinalboard with the body packs and head harness mounted on it.
Figure 11:
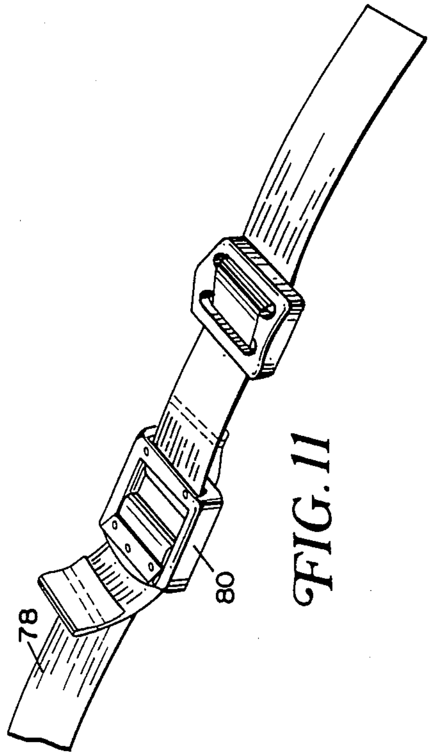
FIG. 11 shows the strap of the right and left side of the head harness.

FIG. 8 also shows the head harness which comprises a lower cushion (60) strapped to the spinalboard (2) through slots (14), (16), (20) and (22) by means of two straps (61) (shown in FIG. 9). The head harness (70) comprises a triangular shaped forehead cushion (72) fitted with restraining straps (74) and (76) at the base and (78) at the top. Each of the straps (74), (76) and (78) has a buckle (80) (shown in FIG. 11), similar in construction to the buckle (42) described earlier which permits the straps (74), (76) and (80) to be snugly tightened about the head of a patient.

Figure 10:
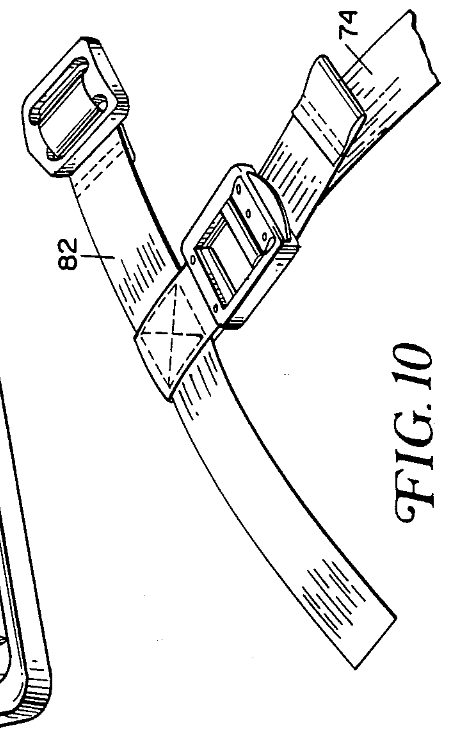
FIG. 10 shows the connection between the straps at the top of the head harness.

Straps (74) and (76) are each connected as illustrated in FIG. 10 with a belt (82). FIG. 10 shows how the connection between belt (74) and a strap (82) is made. Each strap (82) is adapted to be secured to the spinalboard (2) through opening (12) or (18), respectively, and about the outer edge of the corresponding side of the spinalboard. FIG. 9 shows such a connection. For small children it is possible to connect the straps (82) closer to the head by using hole pairs (12) and (14) or (16) and (18) for each strap (82).

Figure 12:
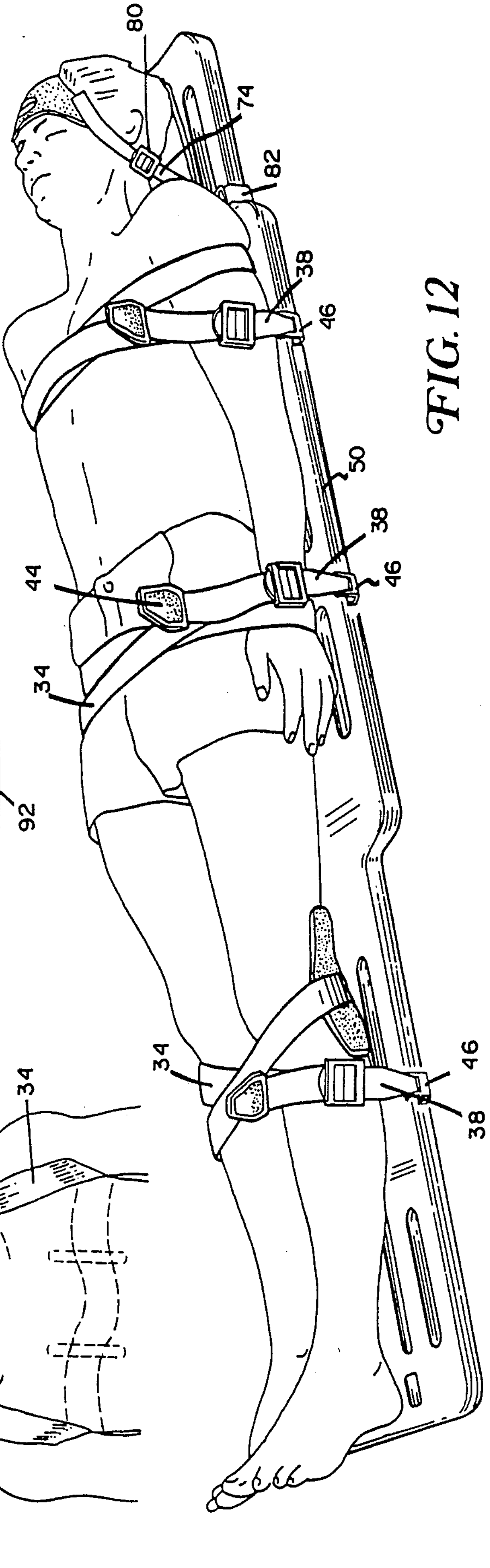
FIG. 12 illustrates a person strapped onto the spinalboard using the body strapping packages and the head harness.
Figure 13:
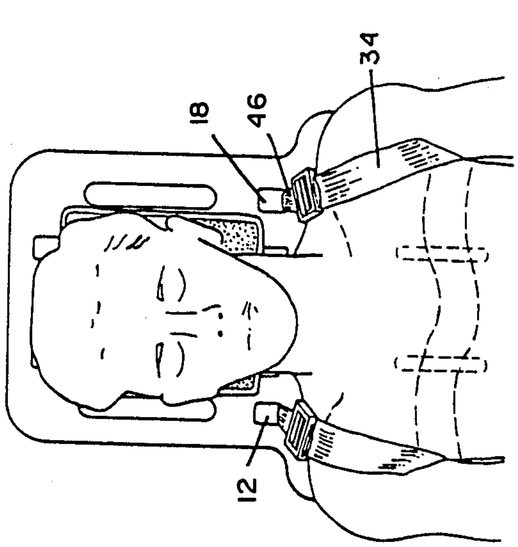
FIG. 13 illustrates a person strapped onto the spinalboard using an alternative over the shoulder method of securement.

FIG. 12 shows an adult strapped in place using the preferred embodiment of this invention using an over the chest method of securement. FIG. 13 shows an accident victim strapped to the board using an over the shoulder method of securement. In FIG. 13 the two hooks (46) of the shoulder straps (34) are passed under the arms of the victim and secured to holes (12) and (18) respectively.

Figure 14:
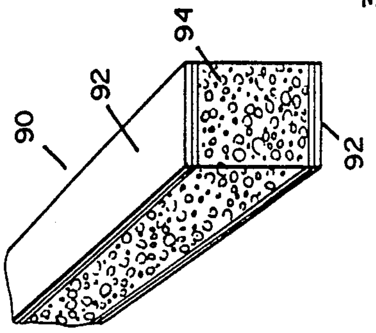
FIG. 14 shows the stiffening beams of this invention.

The stiffening beams (90) of this invention are illustrated in FIG. 14 as comprising two layers of carbon fiber fabrics (92) sandwiching a layer of poly vinyl chloride foam (94). Referring to FIG. 9 showing the bottom of the board (2), the ends (96) are cut after rotomolding the hollow exterior polyethylene shell and two carbon fiber beams (92) are inserted within the runners (26) along their length. The ends (96) are then capped and the board (2) is foam filled. FIG. 5 shows in cross-section the beams (90) within each of the runners (26). The foaming process secures the beams (90) in place and in combination with the board (2) the beams provide rigidity against bending.

The embodiments of the invention in which an exclusive property or privilege is claimed are defined as follows:

1. A spineboard comprising:

a body supporting board having a length and width adapted to support a prostrate person, said board being fabricated of a molded polyethylene hollow shell having one or more stiffening beams inserted within said hollow shell extending lengthwise therealong with remaining portions of said shell being filled with polyurethane foam, said board having a plurality of sets of longitudinally extending tracks at generally longitudinally spaced positions therealong, each set of tracks comprising a pair of slots through the board, said board also having openings at one end;

a head harness comprising a forehead pad and three straps attached to said forehead pad, means for removably securing said straps to said board with each strap being received within a corresponding opening at said one board end;

said harness including slip connectors enabling the straps to be pulled and tightened in one direction and to resist slippage in the other direction whereby said harness is adapted to be tightened over and about the head of an individual to limit movement of the head without interfering with the movement of the chin;

a plurality of body harnesses each comprising a pad overlying a corresponding set of longitudinal tracks on the board and central portions of said board and a strap, means carried by said pad for slidably receiving said strap along the underside of said pad, said strap extending through a pair of slots of said tracks of the board to permit the strap to slide with said pad longitudinally along the set of tracks to a predetermined longitudinal location along said board while enabling the strap to be secured to the board by means of engagement through the slots of said tracks, each said strap of said body harness having two ends, a hook carried by at least one of said strap ends to snap fit over an edge of the board, each said strap having slidable connectors which permit the strap to be drawn tight in one direction while resisting sliding of the strap through the connector in the reverse direction.

2. A spineboard as claimed in claim 1 wherein said forehead pad includes an elastic material.

3. A spineboard as claimed in claim 1 wherein said forehead pad has an opening adapted to fit about a portion of a head to be restrained.

4. A spineboard according to claim 1 wherein each said stiffening beam comprises two layers of carbon fiber fabrics spaced one from the other by a layer of polyvinyl chloride foam.

5. A spineboard according to claim 1 including a pair of transversely spaced longitudinally extending runners extending along the underside of said spineboard and spaced inwardly from the lateral margins of said spineboard, means defining a plurality of handholds disposed at longitudinally spaced positions along the opposite margins of said spineboard laterally outwardly of said runners, said means defining the handholds lying above the elevation of said runners such that the handholds may be conveniently grasped when the spineboard runners rest on a surface.

6. A spineboard according to claim 5 wherein said beams overlie said runners.

7. A spineboard according to claim 6 wherein said spineboard has a lower surface between said runners at an elevation above the elevation of said runners, the straps of said body harness passing through said slots and along said lower surface at an elevation above the runners.

8. A spineboard comprising:

a body supporting board having a length and width adapted to support a prostrate individual, said board being fabricated of a molded polyethylene hollow shell having one or more stiffening beams within said hollow shell and extending lengthwise therealong, with the remaining portions of said shell being filled with polyurethane foam, each of said beams being comprised of two layers of carbon fiber fabrics spaced one from the other by a layer of polyvinyl chloride foam, said board having a plurality of sets of longitudinally extending tracks at generally longitudinally spaced positions therealong, each set of tracks comprising a pair of slots through the board.

9. A spineboard according to claim 8 including a pair of transversely spaced longitudinally extending runners extending along the underside of said spineboard and spaced inwardly from the lateral margins of said spineboard, means defining a plurality of handholds disposed at longitudinally spaced positions along the opposite margins of said spineboard laterally outwardly of said runners, said means defining the handholds lying above the elevation of said runners such that the handholds may be conveniently grasped when the spineboard runners rest on a surface.

10. A spineboard according to claim 9 wherein said beams overlie said runners.

11. A spineboard according to claim 9 wherein said spineboard has a lower surface between said runners at an elevation above the elevation of said runners, a plurality of body harnesses each comprising a pad overlying a corresponding set of longitudinal tracks on the board and central portions of said board and a strap, means carried by said pad for slidably receiving said strap along the underside of said pad, said strap extending through a pair of slots of said tracks of the board to permit the strap to slide with said pad longitudinally along the set of tracks to a predetermined longitudinal location along said board while enabling the strap to be secured to the board by means of engagement through the slots of said tracks, the straps of said body harness passing through said slots and along said lower surface at an elevation above the runners.

* * * * *